US005545135A

United States Patent [19]

Iacob et al.

[11] Patent Number: 5,545,135
[45] Date of Patent: Aug. 13, 1996

[54] PERFUSION BALLOON STENT

[75] Inventors: Mihai Iacob, Bucharest, Romania; Erik C. Andersen, Roskilde, Denmark

[73] Assignee: Boston Scientific Corporation, Natick, Mass.

[21] Appl. No.: 331,999

[22] Filed: Oct. 31, 1994

[51] Int. Cl.⁶ .......................... A61M 31/00; A61M 29/00
[52] U.S. Cl. ........................ 604/96; 604/53; 604/101; 606/195
[58] Field of Search ........................... 604/53, 96, 101, 604/102, 280, 282; 606/192, 194, 195

[56] References Cited

U.S. PATENT DOCUMENTS

| | | |
|---|---|---|
| 4,183,102 | 1/1980 | Guiset . |
| 4,560,374 | 12/1985 | Hammerslag . |
| 4,649,922 | 3/1987 | Wiktor . |
| 4,733,665 | 3/1988 | Palmaz . |
| 4,795,427 | 1/1989 | Helzel . |
| 4,893,623 | 1/1990 | Rosenbluth . |
| 4,909,252 | 3/1990 | Goldberger ........................... 606/194 |
| 4,950,227 | 8/1990 | Savin et al. . |
| 5,000,734 | 3/1991 | Boussignac et al. . |
| 5,002,531 | 3/1991 | Bonzel . |
| 5,078,685 | 1/1992 | Colliver . |
| 5,090,958 | 2/1992 | Sahota . |
| 5,102,402 | 4/1992 | Dror et al. ................................ 604/96 |
| 5,156,620 | 10/1992 | Pigott . |
| 5,167,628 | 12/1992 | Boyles ..................................... 604/101 |
| 5,181,911 | 1/1993 | Shturman . |
| 5,190,058 | 3/1993 | Jones et al. . |
| 5,192,297 | 3/1993 | Hull . |
| 5,192,307 | 3/1993 | Wall . |
| 5,221,261 | 6/1993 | Termin et al. . |
| 5,226,888 | 7/1993 | Arney . |
| 5,242,399 | 9/1993 | Lau et al. . |
| 5,257,974 | 11/1993 | Cox . |
| 5,290,247 | 3/1994 | Crittenden . |
| 5,295,962 | 3/1994 | Crocker et al. . |
| 5,312,339 | 5/1994 | Boussignac et al. . |
| 5,318,535 | 6/1994 | Miraki ..................................... 604/102 |
| 5,334,201 | 8/1994 | Cowan .................................... 606/194 |
| 5,354,309 | 10/1994 | Schnepp-Peach et al. . |
| 5,360,401 | 11/1994 | Turhland ................................. 604/96 |
| 5,364,354 | 11/1994 | Walker et al. ........................... 604/96 |
| 5,470,314 | 11/1995 | Walinsky ................................. 604/96 |

FOREIGN PATENT DOCUMENTS

| | | |
|---|---|---|
| 3640745A1 | 11/1985 | Germany . |
| WO91/07927 | 6/1991 | WIPO . |
| WO92/07606 | 5/1992 | WIPO . |
| WO94/03230 | 2/1994 | WIPO . |

OTHER PUBLICATIONS

ACS RX Perfusion Literature.

*Primary Examiner*—Randall L. Green
*Assistant Examiner*—Anh-Tuan T. Nguyen
*Attorney, Agent, or Firm*—Fish & Richardson P.C.

[57] ABSTRACT

A stent device constructed to reside for a prolonged period in a blood vessel for engagement with the vessel wall while enabling blood flow therethrough. The device includes an elongated stent structure of limited length and sized to wholly reside in the vessel having an inner tubular structural member defining a flow passage and an outer flexible inflatable element constructed to engage the vessel wall at sub-dilation pressure. The passage is sized to fit over a removable transfer element for delivery of the device to a desired site within the vessel. An elongated, flexible inflation-deflation lumen element secured to the inflatable element has an exterior cross-section sufficiently small to permit prolonged residence in the vascular system without substantial adverse effect upon blood flow in the vessel. A method of engaging a vessel wall with the stent device is described.

26 Claims, 7 Drawing Sheets

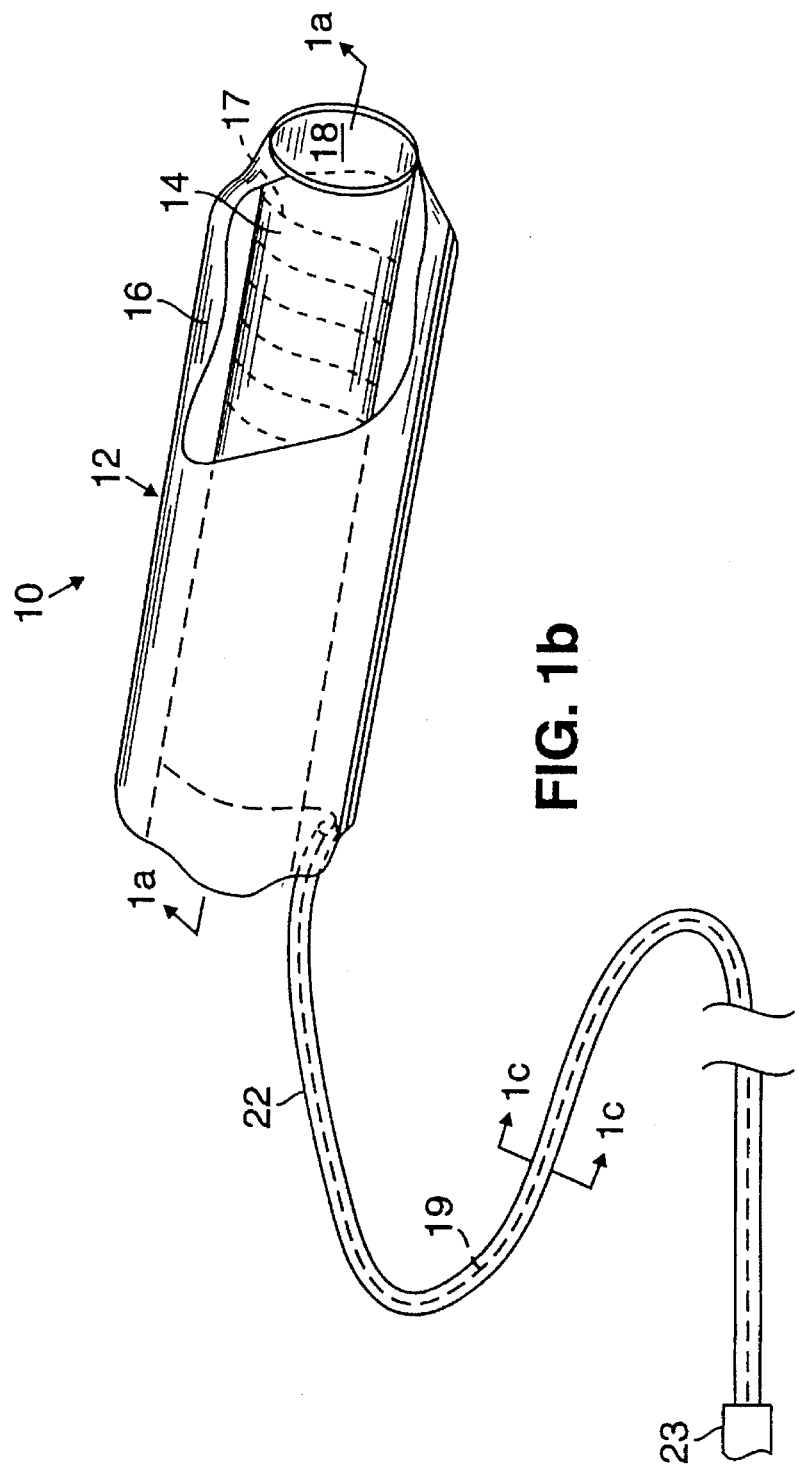
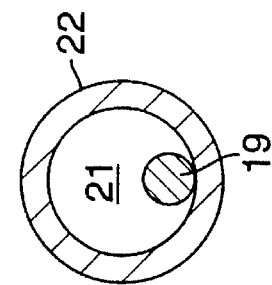
FIG. 1b
FIG. 1c

PERFUSION BALLOON STENT

BACKGROUND OF THE INVENTION

This invention relates to perfusion and temporary stents and has particular application to percutaneous transluminal coronary angioplasty (PTCA) and the ability to address intimal tears resulting from balloon dilatation.

It has been known to inflate the balloon of a perfusion catheter at the site of an intimal tear, thereby applying pressure to the vessel wall in the vicinity of the tear enabling the tear to reattach to the vessel wall. There have been drawbacks to this technique due to practical limits on the dwell time of the catheter at the site of the tear.

SUMMARY OF THE INVENTION

It is realized, according to the invention, that by providing a stent device having a balloon for engagement with a vessel wall while enabling blood flow therethrough and a relatively small cross-section, elongated, flexible inflation-deflation lumen element, dwell time in the vessel is increased.

One aspect of the invention relates to a stent device constructed to reside for a prolonged period in a blood vessel for engagement with the vessel wall while enabling blood flow therethrough. The device includes an elongated stent structure having an inner tubular structural member and an outer flexible inflatable element. The stent structure is of limited length and sized to wholly reside in the vessel. The inner tubular structural member defines an inner passage to enable perfusing blood flow therethrough. The inner passage is sized to fit over a removable transfer element for delivery of the device to a desired site within the vessel. The outer flexible inflatable element is secured about the outer side of the inner tubular structural member and constructed to be inflated to removably engage the vessel wall at sub-dilation pressure. The inner tubular structural member has sufficient radial stiffness to resist collapse when exposed to the inflation pressure whereby the inner passage remains open for the-blood flow when the inflatable element is inflated. The device further includes a relatively small cross-section, elongated, flexible inflation-deflation lumen element secured to the inflatable element. The lumen element is sized to permit passage of inflation fluid while having an exterior cross-section sufficiently small to permit prolonged residence in the vascular system without substantial adverse effect upon blood flow in the vessel. The lumen element extends to an inflation-deflation site outside the body, from which site the inflatable element in inflated state may be deflated when desired.

Preferred embodiments of this aspect of the invention include one or more of the following features:

The stent device is constructed and sized to reside in a coronary artery following a PTCA procedure.

The inner passage is sized and constructed to receive the transfer element in the form of a balloon of a balloon catheter. The internal surface of the tubular member is exposed to be grippably engaged by the balloon of the balloon catheter when the balloon is inflated.

The device and the balloon of the balloon catheter are cooperatively related such that when the balloon is inflated to a selected pressure, the balloon tightly engages the inner tubular structural member to enable the balloon catheter to deliver the device to a desired site within the vessel.

The inner tubular structural member has a proximal opening shaped to enable entry of a balloon catheter when the device is in situ in the vessel of a body, to enable insertion and subsequent inflation of the balloon of the balloon catheter to grip the device to enable the device to be withdrawn from the body.

The inner tubular structural member further includes a spring coil axially disposed on the inner tubular structural member in an axially stiffening relationship for providing radial rigidity to the inner tubular structural member.

The spring coil is a multi-filar coil including a first coil axially disposed on the inner tubular structural member comprising a radiopaque material for providing radiopacity to the inner tubular structural member, and a second coil axially disposed on the inner tubular structural member to provide flexibility and torqueability to the stent device.

The inflation-deflation lumen element has sufficient tensile strength to enable removal of the device from the vessel by pulling on the element.

A tension element is located within the inflation-deflation lumen element for providing the inflation-deflation lumen element with sufficient tensile strength to enable removal of the device from the vessel by pulling on the element.

The tension element is integral with the second coil.

The stent device is constructed and arranged to deliver drugs to a diseased site. The drug is transported to the diseased site through the inflation-deflation lumen, and the outer flexible inflatable element has sufficient permeability to deliver the drug to the diseased site. The drug is transported to the diseased site as a coating on an outer surface of the outer flexible inflatable element.

Another aspect of the invention concerns a method of engaging a vessel wall with a stent device constructed to reside in a vessel for a prolonged period while enabling blood flow therethrough including the steps of providing a device including an elongated stent structure having an inner tubular structural member and an outer flexible inflatable element. The stent structure is of limited length and sized to wholly reside in the vessel. The inner tubular structural member defines an inner passage to enable perfusing blood flow therethrough. The inner passage is sized to fit over a removable transfer element for delivery of the device to a desired site within the vessel. The outer flexible inflatable element is secured about the outer side of the inner tubular structural member and constructed to be inflated to removably engage the vessel wall at sub-dilation pressure. The inner tubular structural member has sufficient radial stiffness to resist collapse when exposed to the inflation pressure whereby the inner passage remains open for the blood flow when the inflatable element is inflated. The device further includes a relatively small cross-section, elongated, flexible inflation-deflation lumen element secured to the inflatable element. The lumen element is sized to permit passage of inflation fluid while having an exterior cross-section sufficiently small to permit prolonged residence in the vascular system without substantial adverse effect upon blood flow in the vessel. The lumen element extends to an inflation-deflation site outside the body, from which site the inflatable element in inflated state may be deflated when desired. An elongated transfer element constructed to removably engage the interior of the stent structure is provided. The device is delivered by manipulating the transfer element to enter the vessel.

Preferred embodiments of this aspect of the invention include one or more of the following features:

The transfer element is a balloon catheter. The balloon of the balloon catheter is sized and constructed to enter the inner tubular structural member when the balloon is deflated, and constructed, when the balloon is inflated, to engage the inner tubular structural member with sufficient force to transfer the stent device.

When it is desired to deliver the device to a vessel, the elongated stent structure is placed over the balloon of the balloon catheter with the distal end of the balloon catheter extending past a distal end of the stent device. The balloon is inflated to a preselected pressure to engage the inner tubular structural member with sufficient force to enable the balloon catheter to deliver the stent device to a vessel. The balloon catheter is advanced through a guiding catheter to deliver the device to the vessel.

When it is desired for the stent device to reside in a vessel while permitting blood flow therethrough, the balloon of the balloon catheter is deflated, the balloon catheter is removed, and the outer flexible inflatable element is inflated through the inflation-deflation lumen element to enable the outer flexible inflatable element to engage the vessel wall.

When it is desired to remove the stent device from a vessel, the balloon catheter is advanced through a guiding catheter to deliver the balloon catheter to the vessel and insert the balloon of the balloon catheter into the inner passage. The balloon of the balloon catheter is inflated to engage the inner tubular structural member with sufficient force to remove the stent device from the vessel. The outer flexible element is deflated through the inflation-deflation lumen element, and the balloon catheter is removed with the stent device from the vessel.

The balloon catheter for delivery and removal of the stent device is used for balloon dilatation of a diseased site prior to delivering the stent device to the diseased site.

The transfer element is a trocar. The trocar includes a bayonet at its distal end, and the inner tubular structural member includes a locking device whereby the bayonet can be locked to the inner tubular structural member for delivery or removal of the stent device. The bayonet is rotatable between the locked position and an unlocked position.

The stent device is constructed and sized to reside in a coronary artery following a PTCA procedure.

The inflation-deflation lumen element has sufficient tensile strength to aid in the insertion of the balloon catheter into the device inner passage by pulling on the element during the balloon catheter advancement into the inner passage.

BRIEF DESCRIPTION OF THE DRAWINGS

FIG. 1a is a side cross-sectional view of the stent device of FIG. 1, taken along the line 1a—1a; FIG. 1b is another perspective view of the stent device incorporating a supporting wire; FIG. 1c is a cross-sectional view of FIG. 1b, taken along line 1c—1c;

DESCRIPTION OF PREFERRED EMBODIMENTS

The figures show stent devices according to the present invention constructed to removably reside in a vessel, e.g., a coronary artery, for engagement with the vessel wall for extended periods while enabling blood flow therethrough.

Figure 1:
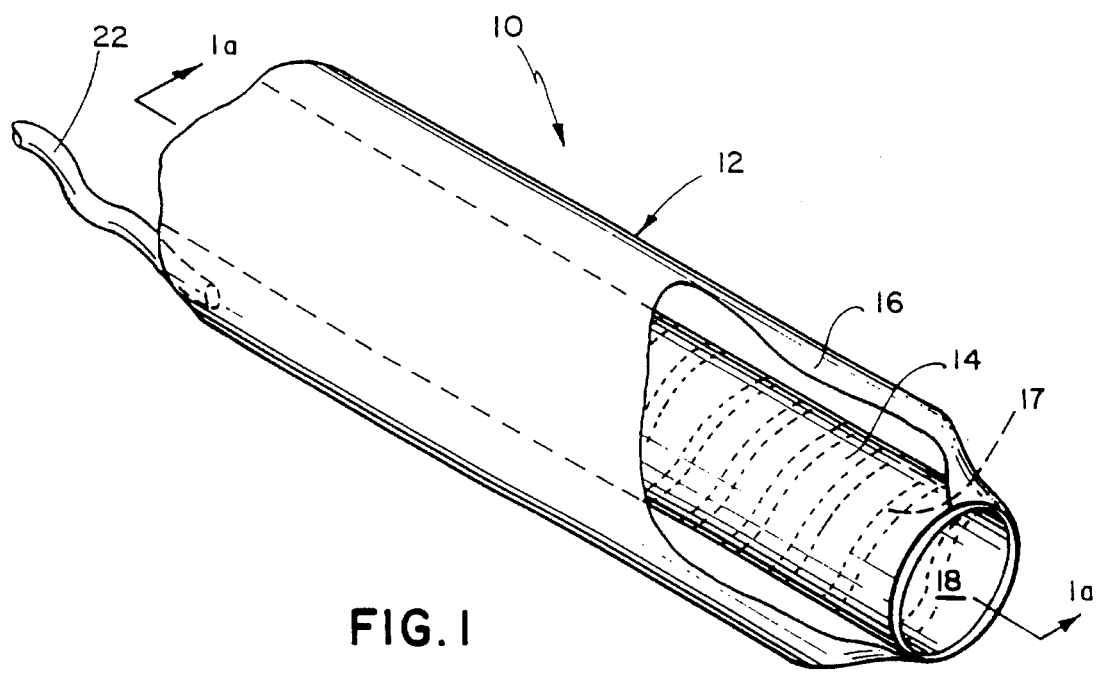
FIG. 1 is a perspective view of a stent device.
Figure 1A:
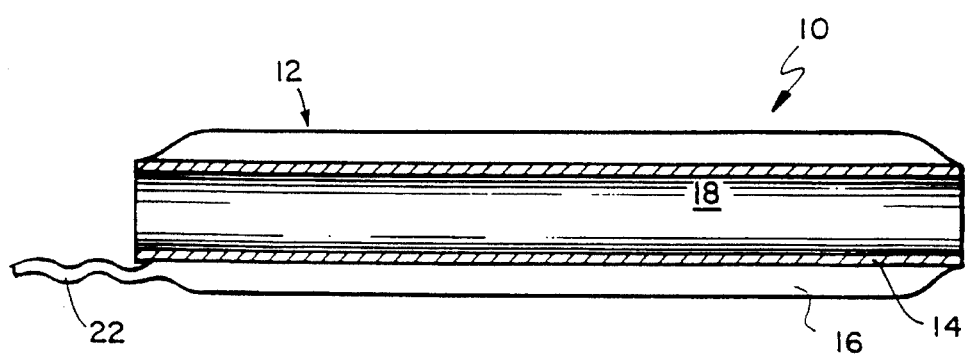

Referring to FIGS. 1–1a, stent device 10 comprises an elongated stent structure 12, e.g., 1.0–5 cm, preferably 2 cm long, and 1.5–5 mm, preferably 2 mm in diameter, and a flexible inflation-deflation lumen element 22, about 140 cm long, and having an inside diameter of about 0.25 mm and an outside diameter of about 0.6 mm. This relatively small outer diameter enables comfortable dwelling of lumen element 22 in the vascular system for extended periods of time.

Stent structure 12 includes inner tubular member 14 and outer flexible inflatable element 16. Inner tubular member 14 defines a large flow passage 18, on the order of 1.2 mm in diameter, for perfusion of high blood flow volumes. Inner tubular member 14 has an overall thickness of about 0.05–0.08 mm, is formed of a polymer, e.g., high density polyethylene or teflon, and has the characteristic of being rigid radially to withstand inflation pressures without collapsing but flexible longitudinally to adapt to curves in an artery.

Inner tubular member 14 need not be formed of a low friction material as it does not pass over a guidewire. This has the advantage of permitting material selection without regard to lubricity. Inner tubular member 14 may incorporate a spring coil 17, e.g., 0.025–0.05 mm flat or round wire, to aid in achieving the desired radial rigidity and longitudinal flexibility. Spring coil 17 may be formed of two parallel coils having the same lead angle and radius. One coil is made of gold to impart radiopacity to inner tubular member 14, and the other coil is made of nitinol to impart flexibility and torqueability to inner tubular member 14.

Spring coil 17 assures that inner tubular member 14 maintains dimensional stability, e.g., does not soften and buckle after prolonged exposure to body temperature or collapse and close off the vessel lumen, and provides tubular member 14 with sufficient radial rigidity to maintain its profile when a PTCA balloon is expanded in flow passage 18, as described below. Any increase in the profile of stent structure 12 due to the expanded PTCA catheter in flow passage 18 could cause device 10 to become caught in a previously inserted guiding catheter during advancement.

Outer flexible inflatable element 16 is bonded to inner tubular member 14. Inflatable element 16 may be formed of a compliant material, e.g., soft nylon, EVA or PE, or of a non-compliant material, e.g., PET, and has a deflated diameter of about 1.5 mm and an inflated diameter in the range of 2.0–5.0 mm. The use of a highly compliant material enables inflatable element 16 to conform to an artery wall at the site of a tear so that all of the tear is compressed against the artery wall. The inflatable element may be inflated to a pressure in the range of 3–15 atmospheres. Low pressure inflation permits the inflatable element to be thin walled, e.g., 0.1 mm, so a lower device profile can be achieved permitting a larger flow passage 18 and thus longer dwell times. Additionally, low pressure inflation allows blood flow in the capillaries at the diseased site and also aids in preventing collapse of inner tubular member 14.

Flexible inflation-deflation lumen element 22 is bonded to the inner wall of inflatable element 16 and is formed, e.g., of PE, PET, nylon, or P-bax (a polyether, polyamid mix forming a block polymer, supplied by Atochemie) with a Shore durometer of about 90A or 55D. Inflation-deflation lumen element 22 extends proximally to a remote inflation-deflation site outside the body. There is no need for inflation-deflation lumen element 22 to be formed of a low friction material because it does not pass over a guidewire. Its small diameter and high flexibility provide for comfortable dwelling in the arterial system for extended periods of time.

Referring to FIGS. 1b and 1c, in one embodiment, inflation-deflation lumen element 22 is constructed with sufficient tensile strength, e.g., by incorporating a supporting wire 19 made from, e.g., nitinol, to permit removal of stent device 10 by pulling element 22 proximally. Supporting wire 19 lies loosely within the lumen 21 of inflation-deflation lumen element 22 and is molded to hub 23. Supporting wire 19 transfers the pulling force to stent structure 12 avoiding stretching or damage to inflation-deflation lumen element 22. Supporting wire 19 may be integral with a round nitinol coil of spring coil 17.

Figure 2:
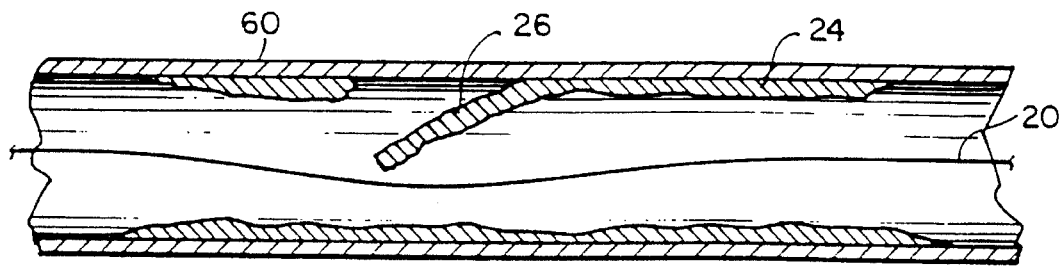
FIGS. 2–2d illustrate the stent device in operation repairing an intimal tear in a coronary artery.
Figure 2A:
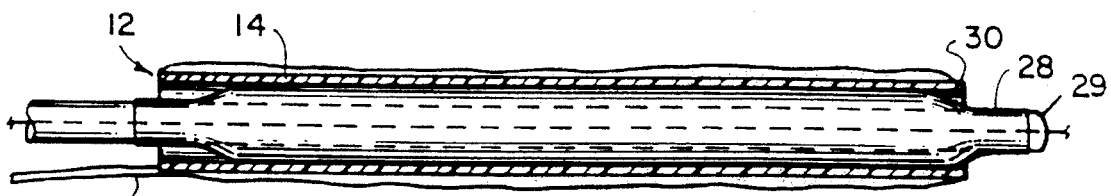

Referring to FIG. 2, in operation, PTCA balloon dilation of a diseased site 24 in an artery 60 is performed resulting in the formation of an intimal tear 26. Referring to FIG. 2a, following the removal of balloon catheter 28 leaving a guidewire 20 in place, elongated stent structure 12 of device 10 is placed over a transfer element, e.g., balloon 30 of balloon catheter 28, with an atraumatic tip 29 of the transfer element extending beyond the distal end of device 10. This significantly reduces the possibility that the distal end of device 10 could cause damage to the vessel wall during advancement.

Figure 2B:
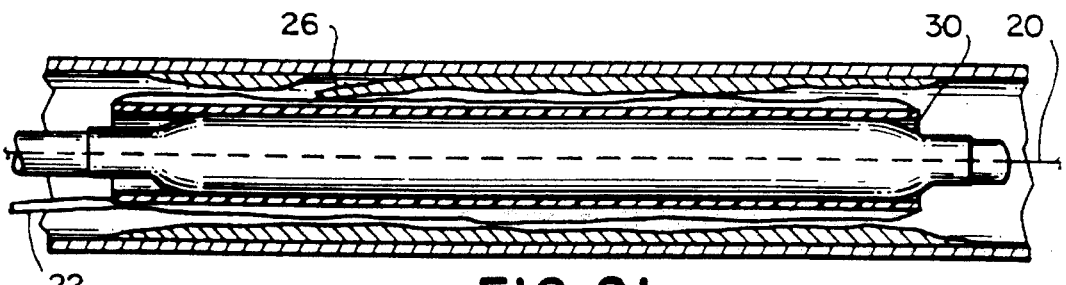

Balloon 30 is inflated to about 5 atmosphere so it engages tubular structural member 14 with sufficient hold to deliver device 10 to diseased site 24. Balloon catheter 28 with elongated stent structure 12 held thereto is advanced through a guiding catheter (not shown) and over guidewire 20 until stent structure 12 is positioned at the site of intimal tear 26, FIG. 2b. A radiopaque marker (not shown) on balloon catheter 28 is used as the indicator for viewing the position of balloon catheter 28 and stent structure 12 with the result that the profile of stent structure 12 can be minimized because additional space is not required for a marker.

Figure 2C:
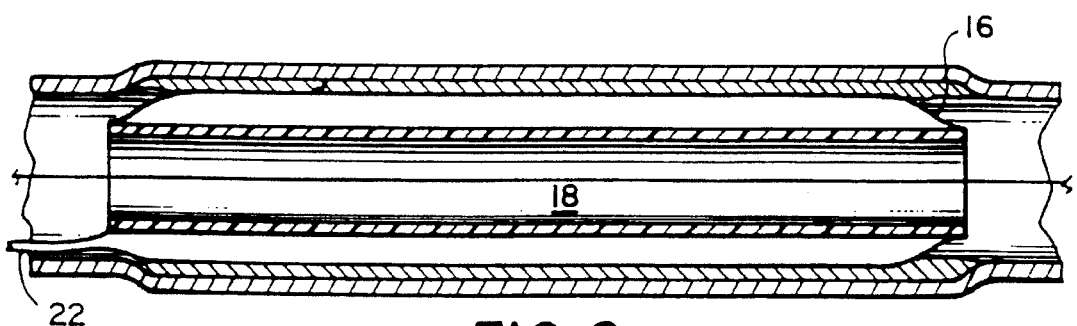

When stent structure 12 is positioned at the site of intimal tear 26, balloon 30 is deflated and balloon catheter 28 removed leaving device 10 in place. Referring to FIG. 2c, inflatable element 16 is then inflated through inflation-deflation lumen element 22 with contrast medium to a pressure in the range of 3–15 atmosphere. Stent device 10 typically remains in place for about fifteen to twenty minutes but could remain in place for several days.

Figure 2D:
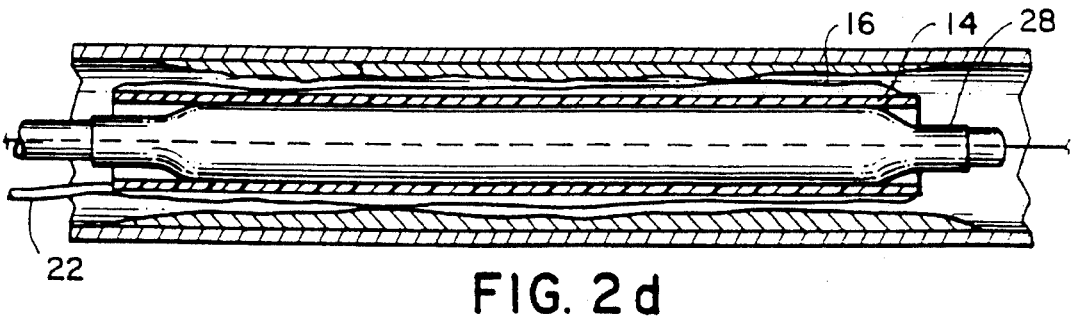

Referring to FIG. 2d, to remove device 10, balloon catheter 28 is reintroduced into flow passage 18 using the radiopaque marker on catheter 28 and the contrast medium in outer flexible element 16 for positioning. Balloon 30 is then inflated to engage inner tubular member 14 and inflatable element 16 is deflated. Catheter 28 with device 10 is then removed by pulling catheter 28 proximally over guidewire 20. The procedure described above can be employed with a balloon catheter designed either for over-the-wire mode or rapid exchange mode.

In another embodiment, inflatable element 16 is used to deliver drugs. Inflatable element 16 may be permeable allowing drugs within the inflation medium to diffuse therethrough or may have an outer drug coating. In this embodiment, device 10 can be used solely as a drug delivery device which permits blood perfusion therethrough, or both as a drug delivery device and a perfusion stent as previously described.

In another embodiment, inflation-deflation lumen element 22 is constructed with sufficient tensile strength to aid in keeping stent structure 12 in place in the vessel while the balloon catheter is reintroduced into flow passage 18 for subsequent removal of device 10.

Figure 3:
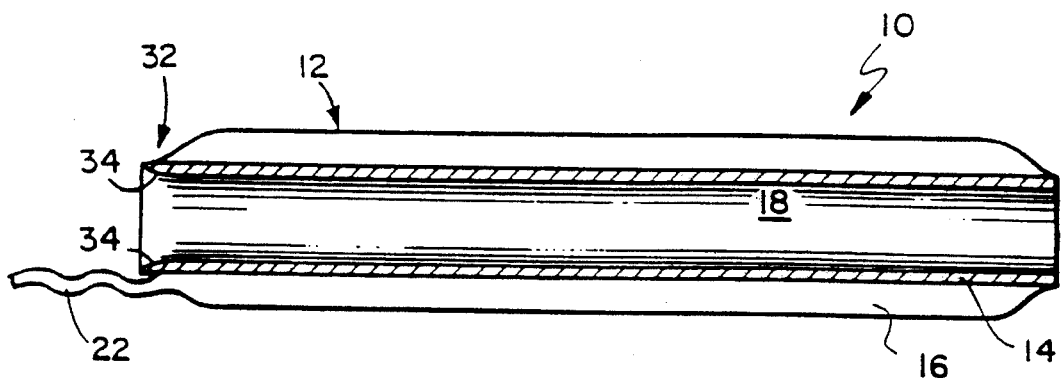
FIG. 3 is a side cross-sectional view of an additional embodiment of the stent device constructed to facilitate the removal of the device from a coronary artery by a balloon catheter.
Figure 3A:
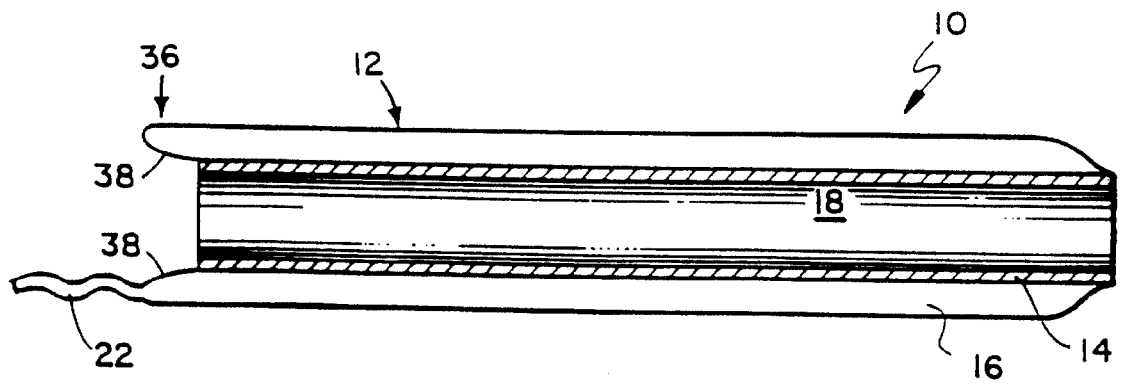
FIG. 3a is a side cross-sectional view of another embodiment of the stent device constructed to facilitate the removal of the device from a coronary artery by a balloon catheter.

In two additional embodiments of device 10, stent structure 12 is shaped to facilitate entry of balloon 30 of balloon catheter 28 into flow passage 18. Referring to FIG. 3, the proximal end 32 of inner tubular member 14 includes flare 34. Alternatively, referring to FIG. 3a, the proximal end 36 of outer flexible inflatable element 16 includes flare 38. When device 10 is to be removed from a coronary artery, the flaring at the proximal end of either inner tubular member 14 or outer flexible inflatable element 16 helps to guide balloon 30 into flow passage 18.

Figure 4:
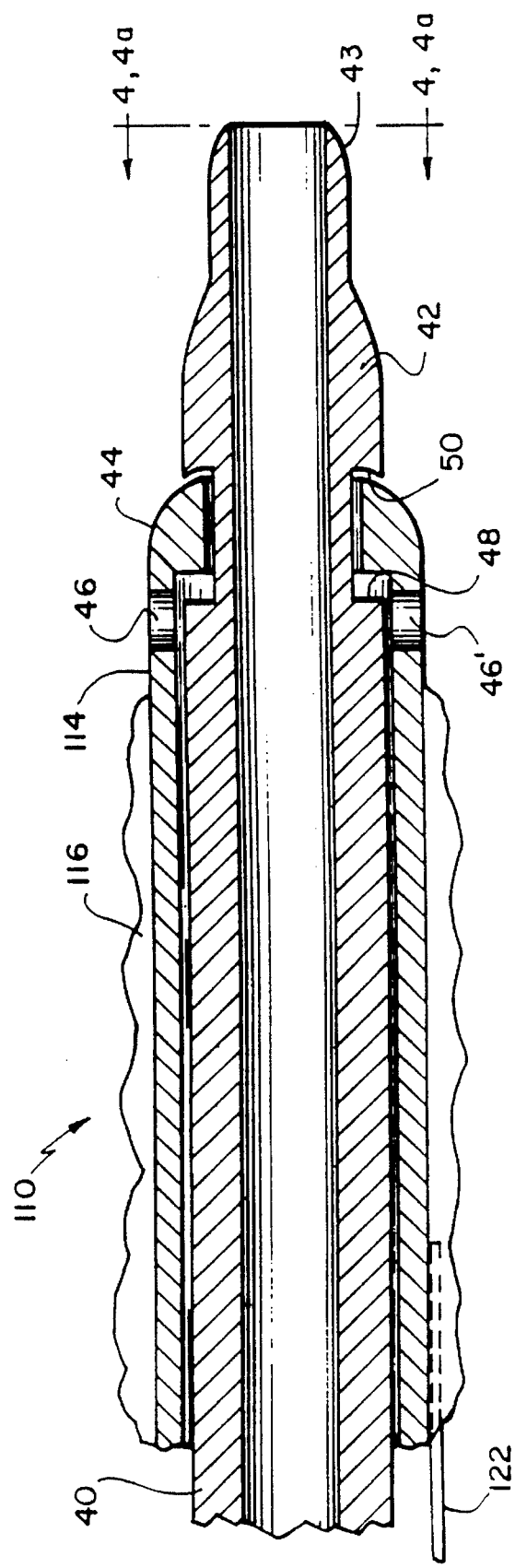
FIG. 4 is a side cross-sectional view of an additional embodiment of the stent device shown mounted on a trocar.

Referring to FIG. 4, in an additional embodiment, the transfer element for the delivery and removal of stent device 110 consists of trocar 40 with bayonet 42 at its distal end. Bayonet 42 includes atraumatic tip 43 for insuring that an atraumatic profile is seen by the vessel wall during advancement. Stent device 110 is constructed as described in the previous embodiment with a modification of inner tubular member 114 to include locking device 44 and perfusion side holes 46, 46'.

Figure 5:
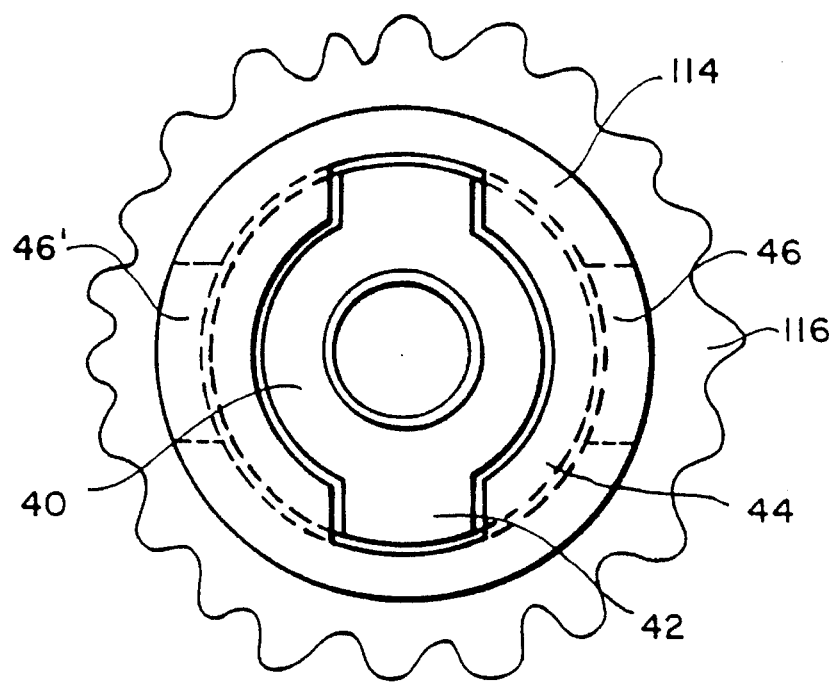
FIGS. 5–5a are end views of the stent device and trocar of FIG. 4, shown with the trocar in unlocked and locked positions, respectively.
Figure 5A:
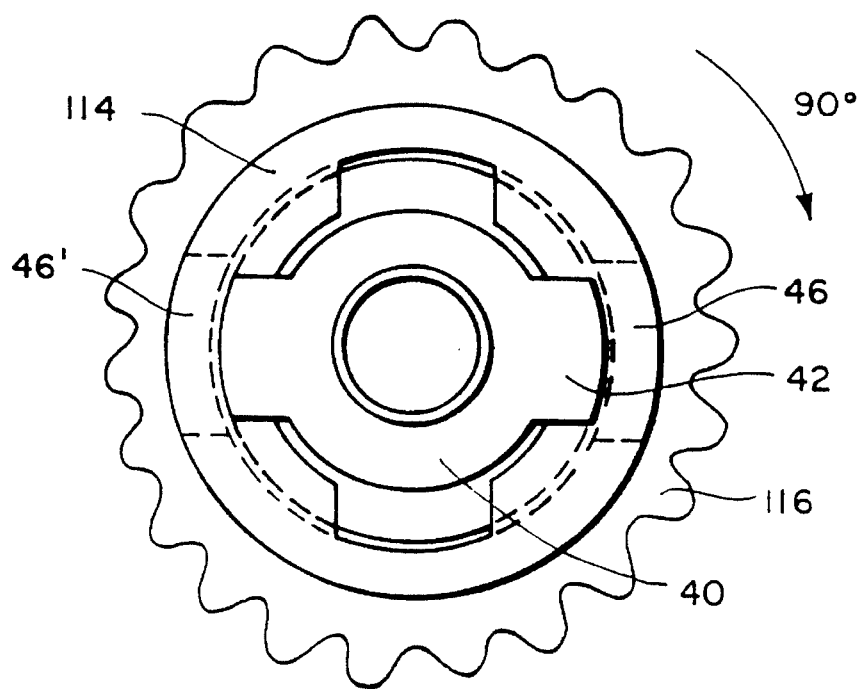

Surface 48 of trocar 40 is constructed to butt against the proximal end of locking device 44 during delivery of device 110 to diseased site 24 and surface 50 of trocar 40 is constructed to butt against the distal end of locking device 44 during removal of device 110. Bayonet 42 can be rotated 90° between an unlocked and a locked position. Referring to FIG. 5, bayonet 42 is shown in its unlocked position in which it enables device 110 and trocar 40 to move axially relative to each other. Referring to FIG. 5a, trocar 40 is shown rotated 90° with bayonet 42 in its locked position preventing relative axial movement between trocar 40 and device 110.

Trocar 40 is made from, e.g., braided high density PE tubing for torqueability or nitinol hypodermic tubing for flexibility and torqueability, with an inner guidewire lumen of diameter about 0.4 mm and an outer diameter of about 0.84 mm.

Figure 6:
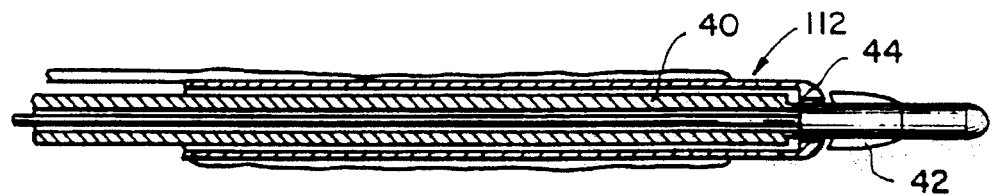
FIGS. 6–6d illustrate the additional embodiment in operation at the site of an intimal tear in a coronary artery.
Figure 6A:
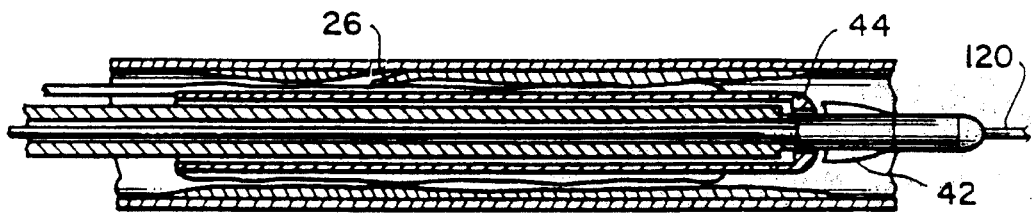
Figure 6B:
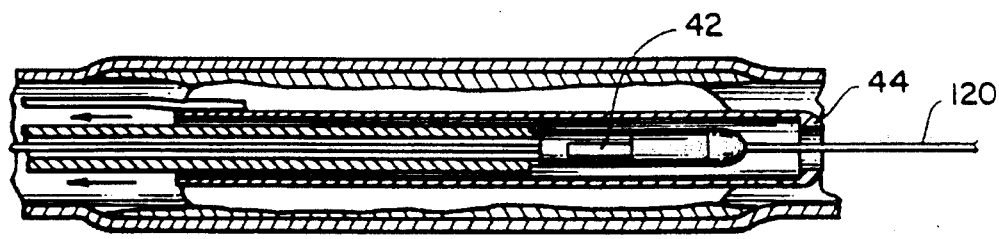
Figure 6C:
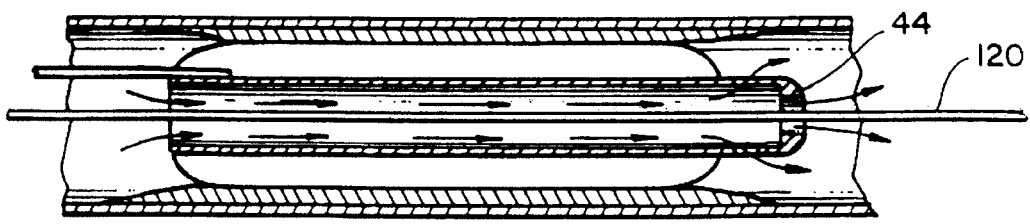
Figure 6D:
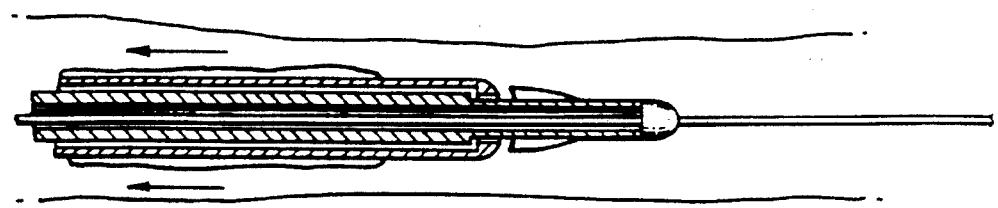

Referring to FIG. 6, in operation, following PTCA balloon dilation resulting in the formation of intimal tear 26, elongated stent structure 112 of device 110 is placed over trocar 40. The trocar is rotated 90° locking the elongated tube in place. Referring also to FIGS. 6a–6d, trocar 40 with device 110 is then advanced over guidewire 120 until device 110 is positioned at the site of intimal tear 26. Inflatable element 116 is then partially inflated through inflation-deflation lumen element 122 with contrast medium to a pressure in the range of 3–15 atmospheres, and trocar 40 is rotated 90° and removed, FIG. 6b, leaving device 110 in place. Inflatable element 116 is then fully inflated, FIG. 6c. Stent device 110 typically remains in place for about fifteen to twenty minutes to repair intimal tear 26 but could remain in place for several days. Referring particularly to FIG. 6d, to remove device 110, trocar 40 is reintroduced over guidewire 120 with bayonet 42 in its unlocked position. It passes through the stent and is then rotated 90° to lock it to locking mechanism 44. Inflatable element 116 is then deflated and trocar 40 with device 110 is removed.

Other embodiments will occur to those skilled in the art and are within the scope of the claims.

What is claimed is:

1. An assembly comprising:

a balloon stent device constructed to reside for a prolonged period in a blood vessel for engagement with the vessel wall while enabling blood flow therethrough, and a removable transfer element for depositing said balloon stent device in said blood vessel, said balloon stent device comprising:

an elongated stent structure comprised of an inner tubular structural member and an outer flexible inflatable element, said stent structure being of limited length, sized to wholly reside in the vessel, said inner tubular structural member defining an inner passage to enable perfusing blood flow therethrough, said inner passage sized to fit over said removable transfer element for delivery of the device to a desired site within the vessel, said outer flexible inflatable element secured about the outer side of said inner tubular structural member and constructed to be inflated to removably engage the vessel wall at sub-dilation pressure, said inner tubular structural member having sufficient radial stiffness to resist collapse when exposed to said inflation pressure whereby said inner passage remains open for said blood flow when said inflatable element is inflated, and a relatively small cross-section, elongated, flexible inflation-deflation element secured to said inflatable element, said inflation-deflation element having an interior lumen sized to permit passage of inflation fluid while having an exterior cross-section sufficiently small to permit prolonged residence of said inflation-deflation element in the vascular system without substantial adverse effect upon blood flow in the vessel, said inflation-deflation element extending to an inflation-deflation site outside the body, from which site said inflatable element in inflated state may be deflated when desired.

2. The assembly of claim 1 wherein said stent device is constructed and sized to reside wholly in a coronary artery following a PTCA procedure.

3. The assembly of claim 1 wherein said removable transfer element comprises a balloon catheter, the internal surface of said tubular member being exposed to be grippably engaged by a balloon of said balloon catheter when said balloon is inflated.

4. The assembly of claim 3 wherein said stent device and the balloon of said balloon catheter are cooperatively related such that when said balloon of said catheter is inflated to a selected pressure, said balloon tightly engages said inner tubular structural member to enable said balloon catheter to deliver said device to a desired site within said vessel.

5. The assembly of claim 3 wherein said inner tubular structural member has a proximal opening shaped to enable entry of the balloon of said balloon catheter when said device is in situ wholly in the vessel of a body, to enable insertion and subsequent inflation of the balloon of said balloon catheter to grip said device to enable the device to be withdrawn from the body.

6. The assembly of claim 1 wherein said inner tubular structural member further comprises a spring coil axially disposed on said inner tubular structural member in an axially stiffening relationship for providing radial rigidity to said inner tubular structural member.

7. The assembly of claim 6 wherein said spring coil is a multi-filar coil including a first coil axially disposed on said inner tubular structural member comprising a radiopaque material for providing radiopacity to said inner tubular structural member, and a second coil axially disposed on said inner tubular structural member to provide flexibility and torqueability to said stent device.

8. The assembly of claim 1 wherein said stent device further comprises a tension element located within said inflation-deflation element for providing said inflation-deflation element with sufficient tensile strength to enable removal of said device from said vessel by pulling on said element.

9. The assembly of claim 8 wherein said inner tubular structural member further comprises a spring coil axially disposed on said inner tubular structural member in an axially stiffening relationship for providing radial rigidity to said inner tubular structural member, said spring coil is a multi-filer coil including a first coil axially disposed on said inner tubular structural member comprising a radiopaque material for providing radiopacity to said inner tubular structural member, and a second coil axially disposed on said inner tubular structural member to provide flexibility and torqueability to said stent device, wherein said tension element is integral with said second coil.

10. The assembly of claim 1 wherein said stent device is constructed and arranged to deliver drugs to a diseased site.

11. The assembly of claim 10 wherein the drug is transported to the diseased site through said inflation-deflation element, and said outer flexible inflatable element has sufficient permeability to deliver the drug to the diseased site.

12. The assembly of claim 10 wherein the drug is transported to the diseased site as a coating on an outer surface of said outer flexible inflatable element.

13. A method of engaging a vessel wall with a balloon stent device constructed to be deposited in a blood vessel of a body by a removable transfer element and to reside in said vessel for a prolonged period while enabling blood flow therethrough, comprising the steps of:

providing said balloon stent device in the form of an elongated stent structure comprised of an inner tubular structural member and an outer flexible inflatable element, said stent structure being of limited length, sized to wholly reside in the vessel, said inner tubular structural member defining an inner passage to enable perfusing blood flow therethrough, said inner passage sized to fit over said removable transfer element for delivery of the device to a desired site within the vessel, said outer flexible inflatable element secured about the outer side of said inner tubular structural member and constructed to be inflated to removably engage the vessel wall at sub-dilation pressure, said inner tubular structural member having sufficient radial stiffness to resist collapse when exposed to said inflation pressure whereby said inner passage remains open for said blood flow when said inflatable element is inflated, and a relatively small cross-section, elongated, flexible inflation-deflation element secured to said inflatable element, said inflation-deflation element having an interior lumen sized to permit passage of inflation fluid while having an exterior cross-section sufficiently small to permit prolonged residence of said inflation-deflation element in the vascular system without substantial adverse effect upon blood flow in the vessel, said inflation-deflation element extending to an inflation-deflation site outside the body, from which site said inflatable element in inflated state may be deflated when desired, providing an elongated transfer element constructed to removably engage the interior of said stent structure, engaging said stent structure with said elongated transfer element, while said stent structure is engaged with said transfer element, delivering said device to a target site within the vessel by advancing said transfer element into the vessel, and thereafter disengaging said transfer element from said stent structure at said site and removing said transfer element while leaving said balloon stent device at said site.

14. The method of claim 13 wherein said transfer element is a balloon catheter, a balloon of said balloon catheter sized and constructed to enter said inner tubular structural member when said balloon is deflated, and constructed, when said balloon is inflated, to engage said inner tubular structural member with sufficient force to transfer said stent device.

15. The method of claim 14, whereby, when it is desired to deliver said device to a vessel, further comprising the steps of:

placing said elongated stent structure over said balloon of said balloon catheter with the distal end of said balloon catheter extending past a distal end of said stent device, inflating said balloon to a preselected pressure to engage said inner tubular structural member with sufficient force to enable said balloon catheter to deliver said stent device to a vessel, and advancing said balloon catheter through a guiding catheter to deliver said device to said vessel.

16. The method of claim 15, whereby, when it is desired for said stent device to reside in a vessel while permitting blood flow therethrough, further comprising the steps of:

deflating said balloon of said balloon catheter, removing said balloon catheter, and inflating said outer flexible inflatable element through said inflation-deflation element to enable said outer flexible inflatable element to engage the vessel wall.

17. The method of claim 16, whereby, when it is desired to remove said stent device from a vessels further comprising the steps of:

advancing said balloon catheter through a guiding catheter to deliver said balloon catheter to said vessel and insert said balloon of said balloon catheter into said inner passage, inflating said balloon of said balloon catheter to engage said inner tubular structural member with sufficient force to remove said stent device from said vessel, deflating said outer flexible element through said inflation-deflation element, and removing said balloon catheter with said stent device from said vessel.

18. The method of claim 17 wherein said balloon catheter for delivery and removal of said stent device is used for balloon dilatation of a diseased site prior to delivering said stent device to said diseased site.

19. The method of claim 13 wherein said transfer element is a trocar, said trocar including a bayonet at its distal end, and said inner tubular structural member further comprises a locking device whereby said bayonet can be locked to said inner tubular structural member for delivery or removal of said stent device, said bayonet being rotatable between the locked position and an unlocked position.

20. The method of claim 13 wherein said stent device is constructed and sized to reside in a coronary artery following a PTCA procedure.

21. The method of claim 17 wherein said inflation-deflation element has sufficient tensile strength to aid in said insertion of said balloon catheter into said device inner passage by pulling on said element during said balloon catheter advancement into said inner passage.

22. The stent device of claim 1 wherein said inflation-deflation element has an outer diameter of about 0.6 mm.

23. The stent device of claim 1 wherein said inflation-deflation element has an inner diameter of about 0.25 mm.

24. The stent device of claim 1 wherein said inflation-deflation element is a flexible tube constructed not to be capable of passing over a guidewire.

25. The method of claim 13 further comprising the step of inflating said inflatable element to engage the vessel wall.

26. The assembly of claim 1 wherein said transfer element is a trocar, said trocar including a bayonet at its distal end, and said inner tubular structural member further comprises a locking device whereby said bayonet can be locked to said inner tubular structural member for delivery or removal of said stent device, said bayonet being rotatable between the locked position and an unlocked position.

* * * * *